(12) United States Patent
Webster et al.

(10) Patent No.: US 8,784,774 B2
(45) Date of Patent: Jul. 22, 2014

(54) LABELED MOLECULAR IMAGING AGENTS AND METHODS OF USE

(75) Inventors: Jack Mathew Webster, Colonie, NY (US); Bruce Fletcher Johnson, Scotia, NY (US); Brian Duh-Lan Lee, Rexford, NY (US); Chittari Pabba, Slingerlands, NY (US); Michael James Rishel, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 140 days.

(21) Appl. No.: 13/234,210

(22) Filed: Sep. 16, 2011

(65) Prior Publication Data

US 2013/0071332 A1 Mar. 21, 2013

(51) Int. Cl.
*A61K 49/04* (2006.01)
*A61K 49/00* (2006.01)

(52) U.S. Cl.
USPC .............................. 424/1.89; 424/9.1; 424/9.4

(58) Field of Classification Search
USPC .................. 424/1.89, 9.1, 9.4; 558/49, 14
See application file for complete search history.

(56) References Cited

U.S. PATENT DOCUMENTS

| | | | |
|---|---|---|---|
| 5,171,563 | A | 12/1992 | Abrams et al. |
| 6,306,911 | B1 | 10/2001 | Wachter et al. |
| 6,953,567 | B2 | 10/2005 | Griffiths |
| 7,196,063 | B1 | 3/2007 | Shirvan et al. |
| 7,211,240 | B2 | 5/2007 | Arbogast et al. |
| 7,279,170 | B2 | 10/2007 | Content et al. |
| 7,902,332 | B2 | 3/2011 | De Jesus et al. |
| 7,906,103 | B2 | 3/2011 | Graupner |
| 2007/0014719 | A1 | 1/2007 | Reading et al. |
| 2009/0022664 | A1 | 1/2009 | Srinivasan et al. |
| 2010/0021379 | A1 | 1/2010 | Lam et al. |
| 2010/0272641 | A1 | 10/2010 | Webster et al. |
| 2010/0310455 | A1 | 12/2010 | Carpenter et al. |
| 2010/0324008 | A1 | 12/2010 | Low et al. |
| 2011/0165076 | A1 | 7/2011 | Dinkelborg et al. |

FOREIGN PATENT DOCUMENTS

| | | | |
|---|---|---|---|
| WO | WO2006096207 | A2 | 9/2006 |
| WO | WO2011/057986 | * | 5/2011 |
| WO | WO2011/057986 | A1 | 5/2011 |
| WO | WO2011061154 | A1 | 5/2011 |

OTHER PUBLICATIONS

Joseph O'Sullivan et al. Incorporation of 3H from delta-(L-alpha-amino[4,5-3H]adipyl)-L-cysteinyl-D[4,4-3H]valine into Isopenicillin N, Biochem. J, 1979, 184, 421-426.*
Trang Pham and William Lubell, A Practicle Enantioselective Synthesis of alpha-amino dicarboxylates. Preparation of D- and L-Aminoadipate, alpha-Aminopimelate, and alpha-Aminosuberate, J. Org. Chem., 1994, 59, 3676-3680.*
Search Report and Written Opinion from corresponding PCT Application No. PCT/US2012/053861 dated Nov. 19, 2012.
Hijarrubia et al., "Domain structure characterization of the multifunctional [alpha]-aminoadipate reductase from Penicillium chrysogenum by limited proteolysis: Activation of [alpha]-aminoadipate does not require the peptidyl carrier protein box or the reduction domain", Journal of Biological Chemistry, vol. 278, No. 10, pp. 8250-8256, Mar. 7, 2003.
Banjac et al., "The Cystine/Cysteine CCycle: A Redox Cycle Regulating Susceptibility Versus Resistance to Cell Death", Oncogene, vol. 27, pp. 1618-1628, 2008.
Bassi et al., "Identification and Characterisation of Human xCT That Co-Expresses, With 4F2 Heavy Chain, the Amino Acid Transport Activity System xc", Pflugers Arch—Cur J Physiol, vol. 442, pp. 286-296, 2001.
Dai et al., "Chemoinformatics Analysis Identifies Cytotoxic Compounds Susceptible to Chemoresistance Mediated by Glutathione and Cystine/Glutamate Transport System xc", J. Med. Chem., vol. 50, pp. 1896-1906, 2007.
Gout et al., "Sulfasalazine, a Potent Suppressor of Lymphoma Growth by Inhibition of the xc Cystine Transporter: A New Action for an Old Drug", Leukemia, vol. 15, pp. 1633-1640, 2001.
Huang et al., "Cystine-Glutamate Transporter SLC7A11 in Cancer Chemosensitivity and Chemoresistance", Cancer, Res, vol. 65, No. 16, pp. 7446-7454, Aug. 15, 2005.
Kim et al., "Human Cystine/Glutamate Transporter: cDNA Cloning and Upregulation by Oxidative Stress in Glioma Cells", Biochimica et Biophysica Acta, vol. 1512, pp. 335-344, 2001.
Lackman et al., "Innate Immune Recognition Triggers Secretion of Lysosomal Enzymes by Macrophages", Traffic, vol. 8, pp. 1179-1189, 2007.
Lo et al., "The xc Cystine/Glutamate Antiporter: A Mediator of Pancreatic Cancer Growth With a Role in Drug Resistance", British Journal of Cancer, vol. 99, pp. 464-472, 2008.
Mawatari et al., "Reactive Oxygen Species Involved in the Glutamate Toxicity of C6 Clioma Cells Via XC Antiporter System", Neuroscience, vol. 73, No. 1, pp. 201-208, 1996.
Patel et al., "Differentiation of Substrate and Non-Substrate Inhibitors of Transport System xc: An Obligate Exchanger of L-Glutamate and L-Cystine", Neuropharmacology, vol. 46, pp. 273-284, 2004.
Plathow et al., "Tumor Cell Metabolism Imaging", The Journal of Nuclear Medicine, vol. 49, No. 6, pp. 43S-63S, Jun. 2008.
Sato et al., "Induction of Cystine Transport Activity in Mouse Peritoneal Macrophages by Bacterial Lipopolysaccharide", Biochem. Journal, vol. 310, pp. 547-551, 1995.
Sato et al., Induction of Cystine Transport Via System xc and Maintenance of Intracellular Glutahione Levels in Pancreatic Acinar and Islet Cell Lines, Biochimica et Biophysica Acta, vol. 1414, pp. 85-94, 1998.
Sato et al., "Cloning and Expression of a Plasma Membrane Cystine/Glutamate Exchange Transporter Composed of Two Distinct Proteins", The Journal of Biological Chemistry, vol. 274, No. 17, pp. 11455-11458, 1999.
Varagnolo et al., "F-Labeled Radiopharmaceuticals for PET in Oncology, Excluding FDG", Nuclear Medicine & Biology, vol. 27, pp. 103-112, 2000.
Wu et al., "Glutathione Metabolism and Its Implications for Health", downloaded from jn.nutrition.org, pp. 489-492, 2003.
Taguchi et al., "Induction of Cystine/Glutamate Transporter in Bacterial Lipopolysaccharide Induced Endotoxemia in Mice", Journal of Inflammation, vol. 4, No. 20, pp. 1-7, 2007.

(Continued)

*Primary Examiner* — Michael G Hartley
*Assistant Examiner* — Jagadishwar Samala
(74) *Attorney, Agent, or Firm* — Eileen B. Gallagher

(57) ABSTRACT

Imaging agents are described that comprise labeled substrates capable of being introduced into cells via the cystine/glutamate antiporter. The substrates may be used for imaging or detecting oxidative stress in cells by introducing the labeled agents into cells via the cystine/glutamate antiporter and subsequent detection.

7 Claims, 3 Drawing Sheets

(56) References Cited

OTHER PUBLICATIONS

Mease et al., "N-[N-[(S)-1,3-Dicarboxypropyl]Carbamoyl]-4[18F]Fluorobenzyl-L-Cysteine, [18F]DCFBC: A New Imaging Probe for Prostate Cancer", Clin Cancer Res, vol. 14, No. 10, pp. 3036-3043, May 15, 2008.

de Bruin et al., "1[3-(2-[18F]Fluoropyridin-3-yloxy)propyl]pyrrole-2,5-dione: Design, Synthesis, and Radiosynthesis of a New [18F]Fluoropyridine-Based Maleimide Reagent for the Labeling of Peptides and Proteins", Biconjugate Chem., vol. 16, pp. 406-420, 2005.

Berndt et al., Labeling of Low-Density Lipoproteins Using the 18F-Labeled Thiol-Reactive Reagent N-[6-(4-[18F]Fluorobenzylidene)Aminooxyhexyl]Maleimide, Nuclear Medicine and Biology, vol. 34, pp. 5-15, 2007.

Poethko et al., "Chemoselective Pre-Conjugate Radiohalogenation of Unprotected Mono- and Multimeric Peptides Via Oxime Formation", Radiochim. Acta, vol. 92, pp. 317-327, 2004.

Koglin et al., "Specific PET Imaging of xc Transporter Activity Using a 18F-Labeled Glutamate Derivative Reveals a Dominant Pathway in Tumor Metabolism", Clinical Cancer Research, Abstract.

Mittra et al., "Studies of the 18F L-Glutamate Derivative BAY 94-9392 in Cancer Patients; A Novel Radiopharmaceutical for PET Imaging", J. Nucl. Med, vol. 52, (Supplement 1): 1900, 2011, Abstract.

Ploessl et al., "Comparison of Cell Uptake of Fluorine-18 Labeled (2S,4R)-4-Fluoro-Glutamine (FGin) and (2S,4R)-4-Fluoro-Glutamic Acid (FGlu)", Nucl. Med, vol. 52, (Supplement 1): 1569, 2011, Abstract.

Baek et al., "First Experience With BAY 94-9392, A Novel F-18 L-Glutamate Derivative, for PET/CT Imaging in Patients With Non-Small Cell Lung and Breast Cancer", . Nucl. Med, vol. 52, (Supplement 1): 195, 2011, Abstract.

Koglin et al., "BAY 94-9392—A Novel F-18 L-Glutamate Derivative for Tumor-Specific PET Imaging", . Nucl. Med, vol. 52, (Supplement 1): 412, 2011, Abstract.

Smolarz et al., "BAY 94-9392: A Novel F-18 Labeled Tumor Specific Probe for PET/CT Imaging—Dosimetry", . Nucl. Med, vol. 52, (Supplement 1): 1465, 2011, Abstract.

* cited by examiner

LABELED MOLECULAR IMAGING AGENTS AND METHODS OF USE

BACKGROUND

The invention relates generally to labeled molecular imaging agents and more particularly to imaging agents that are taken up by the cells via the cystine/glutamate transporter.

The concept of molecular imaging promises specific contrast enhancement of molecular signatures of pathology and requires targetable biomarkers that are specifically regulated in certain pathological indications. While such a specific molecular contrast agent could have great utility for imaging and diagnosing disease; validation of a truly specific biomarker has proven to be very difficult. Even if an agent to such a specific biomarker is created, the market for such an agent will be limited to the prevalence of this indication. Therefore there is great interest in developing molecular contrast agents that can be utilized to image a variety of pathological indications. Most imaging agents target specific tissue or cell types, or specific therapies, or they degrade rapidly over time. One example of an agent that is directed at broader applications is $^{18}$F-fluorodeoxyglucose (FDG) that makes use of the glucose transporter. $^{18}$F-FDG is preferentially taken up by cells that have an increased requirement for glucose, and then is trapped inside the cell. FDG can be used clinically for the diagnosis, staging and monitoring of many cancers as well as monitoring metabolism in the heart and brain. $^{18}$F-FDG is not a substrate for sodium-dependent glucose transporters found in the kidney tubules, which prevents its renal resorption and enhances clearance In vivo oxidative stress is recognized as an indicator of cellular stress. Efforts to image this stress have involved imaging animals using electron paramagnetic resonance (EPR). EPR is a technique for detecting unpaired electrons as would occur with the creation of free radicals in oxidative stress. Essentially an agent is used which is considered to be an EPR probe which is sensitive to organ antioxidative activity as a measure of oxidative stress.

Others have looked at using a 13-C-glycine chemical shift MRI to detect glycine uptake and conversion to glutathione in an animal model of chemotherapy treatment of tumors in vivo. Still others, having developed imaging agents to detect apoptotic cells in vivo for monitoring chemotherapy treatment (e.g. labeled Annexin V which is a rather large protein, Aposense by Neurosurvival Technologies which is a family of small molecules which is reported to enter specifically into only apoptotic cells.

Also reported are imaging agents that take advantage of the cellular amino acid transporter (cystine/glutamate antiporter, $x_c^-$), which is activated under conditions of cellular oxidative stress. This is described in U.S. patent application Ser. No. 12/430,573 entitled "Labeled Molecular Imaging Agents, Methods of Making and Methods of Use" and filed on Apr. 27, 2009, which is incorporated herein by reference.

It may also be advantageous to exploit the cystine/glutamate antiporter transport mechanism using other substrates which take advantage of the transport mechanism. As such small molecules that compete with cystine for uptake may be good candidates for imaging agents. Furthermore, the competing mechanism may provide information related to the condition of the cell or its tissue related to its metabolism. Therefore the use of labeled molecules that compete with cystine may provide a valuable tool for identifying tumor types used to design effective treatment therapies.

BRIEF DESCRIPTION

The imaging agents and methods of the invention take advantage of the cellular amino acid transporter (cystine/glutamate antiporter, $x_c^-$) which is activated under conditions of cellular oxidative stress. Additionally, the upregulation of the cystine/glutamate transporter is also associated with chemotherapy resistance in some tumors. Therefore, non-invasive imaging of tumors with high cystine uptake could result in identification of tumors likely to be resistant to certain therapies; which could result in efficacious changes in treatment regimens.

An embodiment of the invention, comprises An imaging agent comprising a $^{18}$F or $^3$H labeled derivative of Formula I

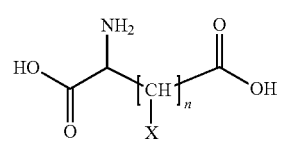

wherein X is independently at each occurrence H, —(CH$_2$)$_m$H, or —O—(CH$_2$)$_m$H; n is an integer between 3 and 7; and m is an integer between 1 and 3.

Another embodiment of the invention comprises a method of imaging cells using a $^{18}$F or $^3$H labeled derivative of Formula I. An example of the method generally comprises, introducing into the target an imaging agent comprising $^{18}$F or $^3$H labeled derivative of Formula I via the cystine/glutamate transporter; and detecting the imaging agent using one or more of, positron emission tomography (PET), autoradiography, scintillation detection, or a combination thereof.

Still another embodiment comprises a method of detecting oxidative stress in cells by introducing the $^{18}$F or $^3$H labeled derivative of Formula I via the cystine/glutamate transporter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
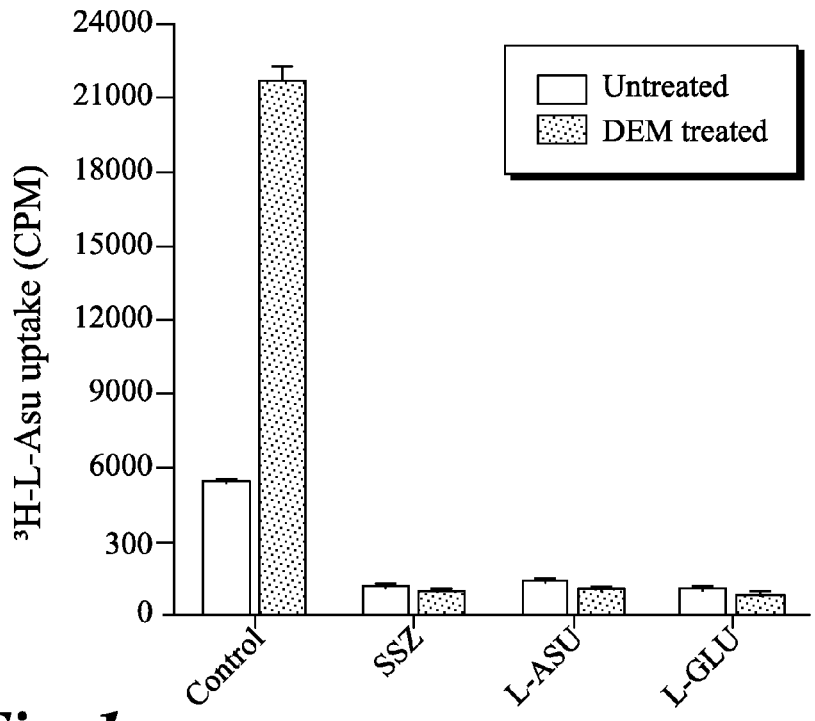
FIG. 1 shows that $^3$H-L-Asu ($^3$H-L-aminosuberic acid) uptake is increased in cells exposed to oxidative stress via DEM treatment.

To more clearly and concisely describe and point out the subject matter of the claimed invention, the following definitions are provided for specific terms, which are used in the following description and the appended claims.

As used herein, the term "cystine/glutamate transporter" are used interchangeably with, and include, the terms cystine/glutamate antiporter, cystine/glutamate exchanger, cystine transporter, $x_c^-$, xc(−), Xc(−), system xc(−), and amino acid transport system Xc(−). The transport system comprises dimer of two proteins and includes, but is not limited to: protein xCT (SLC7A11) and protein CD98 (4F2hc, heavy chain of the 4F2 surface antigen, SLC3A2); protein xCT which is the subunit specific to the xc(−) system; protein CD98 which is a subunit common to a number of transporters with different substrates; and protein xCT that may also dimerize with rBAT, another subunit common to multiple transporters. Also the notations L-ASU and L-Asu both correspond to L-aminosuberic acid.

The cystine/glutamate transporter is not typically expressed or has extremely low expression in most tissues, but is upregulated in cells exposed to oxidative stress. Cystine, which comprises two disulfide-linked cysteine amino acids, is a natural substrate for this transporter. The effect of upregulation of the transporter is an increase in cystine uptake; which is then reduced to cysteine inside the cell. Intracellular cysteine is the rate limiting substrate for glutathione synthesis. Glutathione is the cells primary anti-oxidant to defend against oxidative stress. Intracellular cysteine is incorporated into one of two pathways, glutathione synthesis or protein synthesis.

Generally, the imaging agents of the invention comprise labeled analogs of amino substituted $C_6$-$C_{10}$ dicarboxylic acids that maintain the attributes necessary to be a substrate of the cystine/glutamate antiporter. The analogs are represented by a radioisotopic label derivative of Formula I,

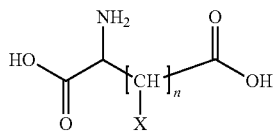

I wherein;

X is independently at each occurrence H, —(CH$_2$)$_m$H, or —O—(CH$_2$)$_m$H, n is an integer between 3 and 7; and m is an integer between 1 and 3.

In certain embodiments Formula I comprises aminosuberic acid.

The imaging agents may be detected by its emitted signal, such as autofluorescence emission or optical properties of the agent. The method of detection of the compounds may include, but are not necessarily limited to, nuclear scintigraphy, positron emission tomography ("PET"), single photon emission computed tomography ("SPECT"), magnetic resonance imaging, magnetic resonance spectroscopy, computed tomography, or a combination thereof depending on the intended use and the imaging methodology available to the medical or research personnel.

The labeled substrates of the invention for the cystine/glutamate transporter may also be used to introduce labeled compounds, such as, but not limited to, an agent of Formula I labeled with $^{18}$F or $^{3}$H, into a target for therapeutic purposes. As used herein target may refer to a cells or tissues of a living subject (in vivo) or isolated (ex vivo).

In certain embodiments, a $^{18}$F or $^{3}$H label will be located on an alkyl group of the carbon chain as represented by Formula II

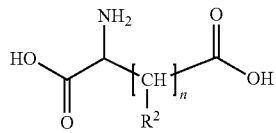

II wherein R$^2$ is independently at each occurrence H, $^{18}$F, $^{3}$H, —(CH$_2$)$_m$R$^3$, or —O—(CH$_2$)$_m$R$^3$:

R$^3$ is $^{18}$F or $^{3}$H:

n is an integer between 3 and 7; and m is an integer between 1 and 3.

In certain embodiments, the compound of Formula II is a single-label compound wherein a single radioisotope label is disposed along the alkyl backbone. It is understood that the position of the radioisotope label may be positioned anywhere along the carbon chain. In certain other embodiments, the compound may be labeled at multiple locations along the alkyl chain.

Table 1 provides representative non-limiting examples of the labeled compounds.

TABLE 1

Representative Examples

Backbone 8 carbon chain

Alkyl substituted, 8 carbon chain

TABLE 1-continued

Representative Examples

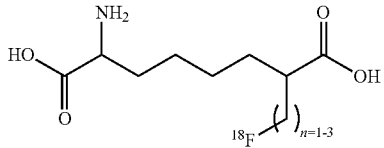
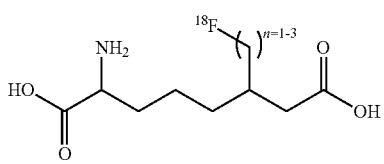
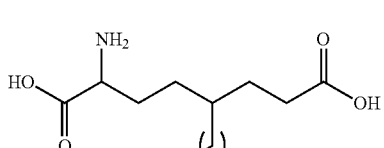
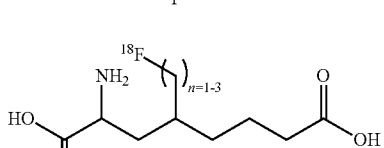
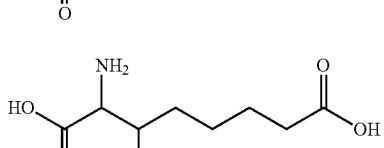

Substituted alkyl ether, 8 carbon chain

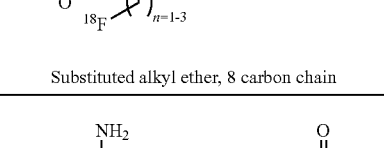
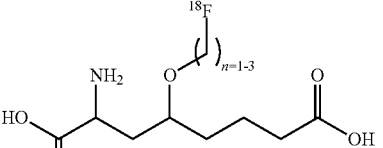
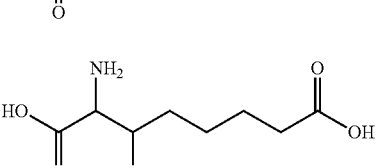

TABLE 1-continued

Representative Examples

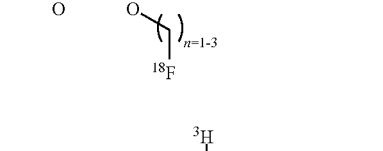
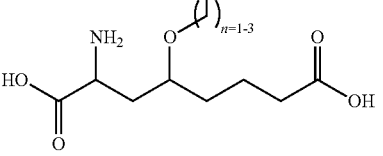
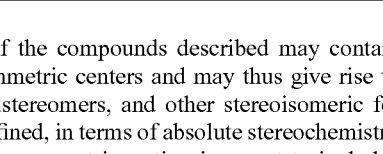

Many of the compounds described may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques.

Unlike other cystine, when the labeled compounds are transported into the cell, they may not be incorporated into the protein synthesis or glutathione synthesis pathways. While it is possible that the compound could be transported out of the cell via the same transporter; the intracellular concentration of L-Glutamate is extremely high and therefore would be the favored substrate for cellular export, resulting in trapping of the majority of the compound in the cells.

In a wide variety of human tissues and cells examined, the $x_c^-$ transporter is predominantly expressed in brain, but also in pancreas and in cultured cell lines. The $x_c^-$ transporter expression is very low in most tissues, but can be upregulated under conditions of oxidative stress and when cells are grown in culture. The $x_c^-$ transporter is induced under a number of conditions, including apoptotic stimuli, oxidative stress, inflammation, cystine deprivation and chemotherapy resistance. For example, $^{18}F$, may be used for in vivo PET imaging, as well as in vitro detection of cellular oxidative stress.

Similarly the upregulation of the cystine/glutamate transporter is also associated with chemotherapy resistance in some tumors. Therefore, non-invasive imaging of tumors with high cystine uptake could result in identification of tumors likely to be resistant to certain therapies; which could result in efficacious changes in treatment regimens.

Following are non-limiting examples used to illustrate various embodiments of the imaging agents and methods of use.

Experimental Procedures:

Scheme 1:

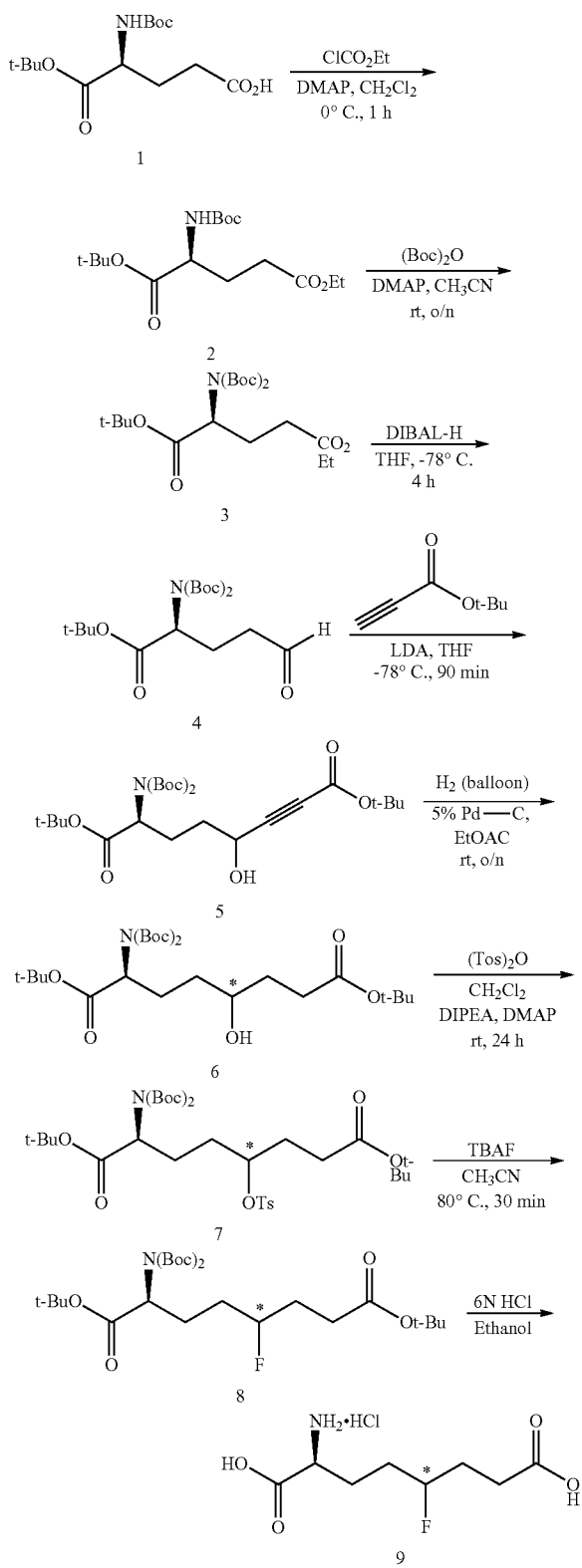

Experimental Procedures:

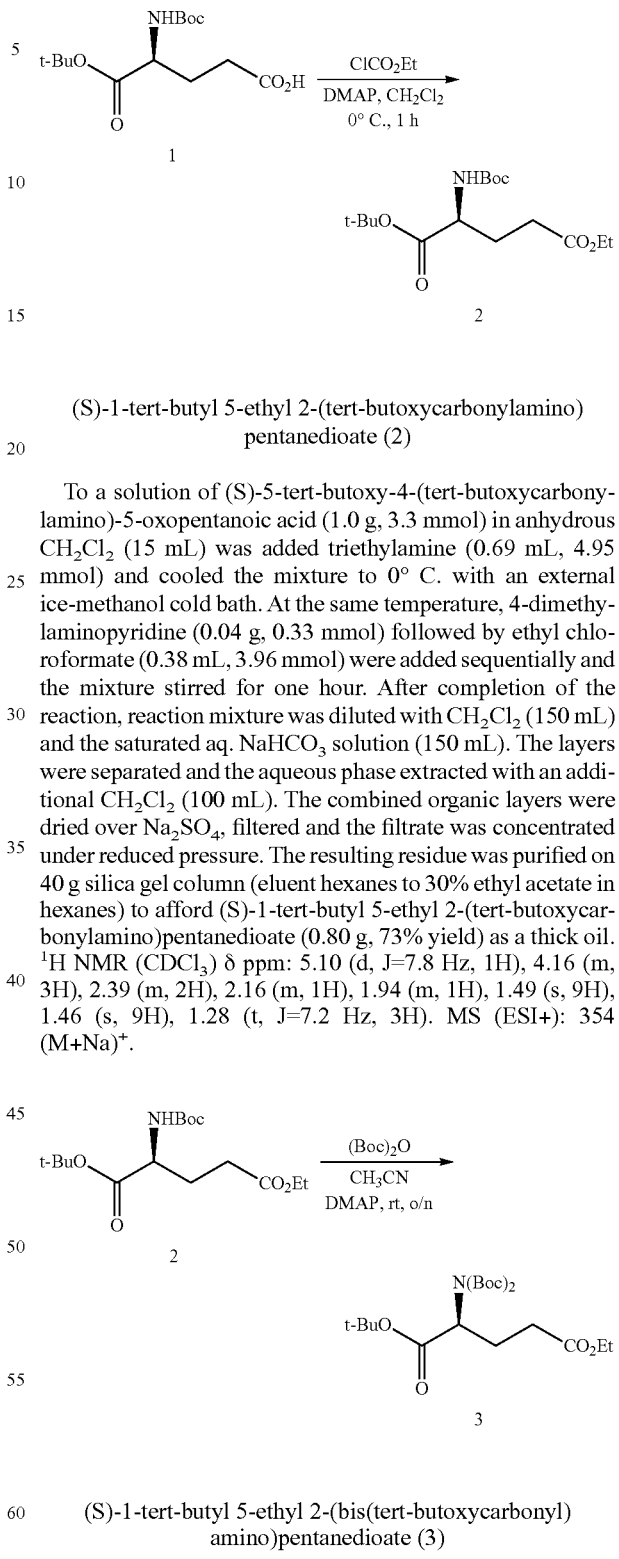

(S)-1-tert-butyl 5-ethyl 2-(tert-butoxycarbonylamino) pentanedioate (2)

To a solution of (S)-5-tert-butoxy-4-(tert-butoxycarbonylamino)-5-oxopentanoic acid (1.0 g, 3.3 mmol) in anhydrous $CH_2Cl_2$ (15 mL) was added triethylamine (0.69 mL, 4.95 mmol) and cooled the mixture to 0° C. with an external ice-methanol cold bath. At the same temperature, 4-dimethylaminopyridine (0.04 g, 0.33 mmol) followed by ethyl chloroformate (0.38 mL, 3.96 mmol) were added sequentially and the mixture stirred for one hour. After completion of the reaction, reaction mixture was diluted with $CH_2Cl_2$ (150 mL) and the saturated aq. $NaHCO_3$ solution (150 mL). The layers were separated and the aqueous phase extracted with an additional $CH_2Cl_2$ (100 mL). The combined organic layers were dried over $Na_2SO_4$, filtered and the filtrate was concentrated under reduced pressure. The resulting residue was purified on 40 g silica gel column (eluent hexanes to 30% ethyl acetate in hexanes) to afford (S)-1-tert-butyl 5-ethyl 2-(tert-butoxycarbonylamino)pentanedioate (0.80 g, 73% yield) as a thick oil. $^1H$ NMR ($CDCl_3$) δ ppm: 5.10 (d, J=7.8 Hz, 1H), 4.16 (m, 3H), 2.39 (m, 2H), 2.16 (m, 1H), 1.94 (m, 1H), 1.49 (s, 9H), 1.46 (s, 9H), 1.28 (t, J=7.2 Hz, 3H). MS (ESI+): 354 $(M+Na)^+$.

(S)-1-tert-butyl 5-ethyl 2-(bis(tert-butoxycarbonyl)amino)pentanedioate (3)

To a mixture of (S)-1-tert-butyl 5-ethyl 2-(tert-butoxycarbonylamino)pentanedioate (1.5 g, 4.52 mmol) and 4-dimethylaminopyridine (DMAP, 0.11 g, 0.90 mmol) in acetonitrile (45 mL) was added excess di-tert-butyldicarbonate (3.0 g, 13.75 mmol) at room temperature. The mixture was stirred for an overnight at the same temperature. Then added another 1.0 g of di-tert-butyldicarbonate (since the starting material was not consumed completely) and stirred for six more hours to drive the reaction towards product formation. After completion of the reaction, solvent was removed under reduced pressure and the crude product was purified on 40 g, silica gel column (eluent hexanes to 20% ethyl acetate in hexanes) to afford (S)-1-tert-butyl 5-ethyl 2-(bis(tert-butoxycarbonyl)amino)pentanedioate (1.76 g, 90.2% yield) as a colorless thick oil. $^1$H NMR (CDCl$_3$) δ ppm: 4.81 (dd, J=5.2, 4.8 Hz, 1H), 4.15 (q, J=7.2 Hz, 2H), 2.41 (m, 3H), 2.16 (m, 1H), 1.52 (s, 18H), 1.47 (s, 9H), 1.27 (t, J=7.2 Hz, 3H). $^{13}$C NMR (CDCl$_3$) δ ppm: 172.8, 169.3, 152.3, 82.9, 81.3, 60.4, 58.1, 31.02, 28.0, 27.9, 24.6 and 14.2. MS (ESI+): 454 (M+Na)$^+$.

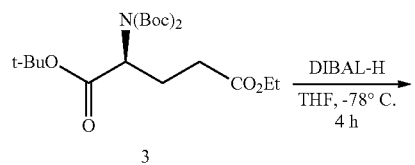

(S)-tert-butyl 2-(bis(tert-butoxycarbonyl)amino)-5-oxopentanoate (4)

A solution of (S)-1-tert-butyl 5-ethyl 2-(bis(tert-butoxycarbonyl)amino)pentanedioate (1.7 g, 3.93 mmol) in dry tetrahydrofuran (30 mL) was cooled to −78° C. with acetone/dry ice bath and added diisobutylaluminum hydride (1.0 M in hexanes 5.9 mL, 5.90 mmol) dropwise over the period of 5 minutes. The reaction was complete after stirring for four hours, then quenched with water (1.5 mL) and allowed to warm to room temperature by removing the external cold bath. The resulting white thick solution was filtered through celite powder and washed with diethyl ether (200 mL). The filtrate was concentrated under reduced pressure and purified on 40 g silica gel column (eluent hexanes to 20% ethyl acetate in hexanes) to afford (S)-tert-butyl 2-(bis(tert-butoxycarbonyl)amino)-5-oxopentanoate (0.90 g, 59.1% yield) as a thick oil. $^1$H NMR (CDCl$_3$) δ ppm: 9.79 (s, 1H), 4.77 (dd, J=9.3, 5.2 Hz, 1H), 2.52 (m, 3H), 2.16 (m, 1H), 1.52 (s, 18H), 1.47 (s, 9H). $^{13}$C NMR (CDCl$_3$) δ ppm: 201.2, 169.2, 152.4, 83.1, 81.5, 58.11, 40.7, 28.0, 27.9 and 21.9. MS (ESI+): 410 (M+Na)$^+$.

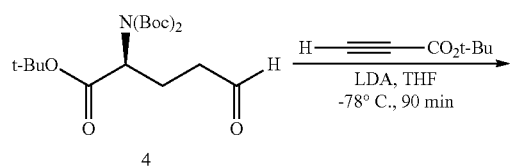

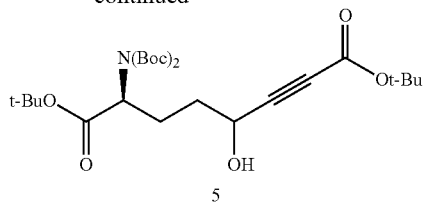

(7S)-di-tert-butyl 7-(bis(tert-butoxycarbonyl)amino)-4-hydroxyoct-2-ynedioate (5)

To a solution of tert-butyl propiolate (42.7 mg, 0.34 mmol) in a dry THF (1.5 mL) was slowly added lithium diisopropylamide (2.0 M in THF/ethyl benzene, 0.15 mL, 0.29 mmol) at −78° C. under nitrogen atmosphere. The resulting reaction mixture was continued stirring at the same temperature for 1.0 hour (to generate lithium propiolate anion), then slowly added (S)-tert-butyl 2-(bis(tert-butoxycarbonyl)amino)-5-oxopentanoate (0.075 g, 0.193 mmol) in 1.0 mL THF solution. The mixture was stirred at the same temperature for 90 minutes (until finished by TLC). Then, the reaction was quenched with saturated aqueous NH$_4$Cl (0.5 mL) solution and warmed to room temperature by removing the external acetone/dry ice bath. The reaction solution was diluted with ethyl acetate (20 mL) and an aqueous saturated solution of NH$_4$Cl (15 mL) was added with stirring. The aqueous phase was extracted with ethyl acetate (50 mL) and the combined organic layers dried and concentrated under reduced pressure. The resulting residue was purified on 12 g silica gel column (eluent, hexanes to 40% ethyl acetate in hexanes) to afford (7S)-di-tert-butyl 7-(bis(tert-butoxycarbonyl)amino)-4-hydroxyoct-2-ynedioate (diastereomeric mixture, 40 mg, 40.3% yield) as an oil. $^1$H NMR (CDCl$_3$) δ ppm: 4.76 (dt, J=9.2, 5.2 Hz, 1H), 4.53 (m, 1H), 2.27 (m, 1H), 2.04 (m, 1H), 1.83 (m, 2H), 1.52 (s, 18H), 1.50 (s, 9H), 1.46 (s, 9H). $^{13}$C NMR (CDCl$_3$) δ ppm: 169.63, 169.52, 152.47, 152.40, 152.34, 84.96, 84.94, 83.63, 83.09, 83.04, 81.48, 81.46, 77.89, 77.84, 61.90, 61.37, 58.47, 58.31, 33.75, 33.70, 28.02, 27.96, 27.93, 25.13 and 24.72. MS (ESI+): 536 (M+Na)$^+$.

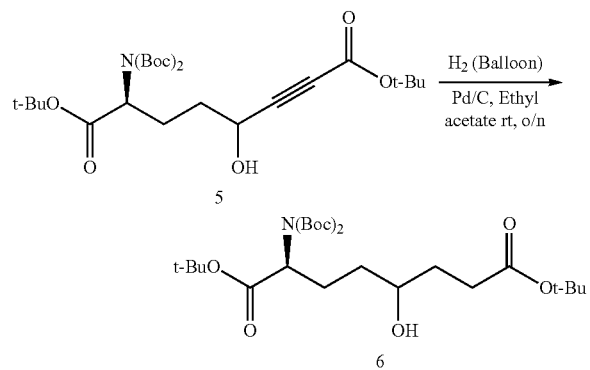

(2S)-di-tert-butyl 2-(bis(tert-butoxycarbonyl)amino)-5-hydroxyoctanedioate (6)

A 25-mL round bottom (RB) flask was purged with nitrogen and charged with (7S)-di-tert-butyl 7-(bis(tert-butoxycarbonyl)amino)-4-hydroxyoct-2-ynedioate (0.04 g, 0.08 mmol), ethyl acetate (5 mL) and 5% palladium on carbon (~2.0 mg dry weight). The RB flask was evacuated, charged with hydrogen gas in a balloon (to a pressure of 13 psi or approximately 1.0 atmosphere pressure) and stirred for an overnight at room temperature. After this time, the hydrogen was evacuated and nitrogen charged into the RB flask. The catalyst was removed by filtration through a pad of Celite 545 and the filter cake washed with ethyl acetate (10 mL). The filtrate was concentrated under reduced pressure to afford (2S)-di-tert-butyl 2-(bis(tert-butoxycarbonyl)amino)-5-hydroxyoctanedioate (diastereomeric mixture, 0.04 g, 99.3% yield) as an oil. $^1$H NMR (CDCl$_3$) δ ppm: 4.73 (m, 1H), 3.63 (m, 1H), 2.37 (m, 2H), 2.27-1.56 (m, 6H), 1.51 (s, 18H), 1.45 (2s, 18H). $^{13}$C NMR (CDCl$_3$) d ppm: 173.60, 173.58, 170.01, 169.75, 152.58, 152.48, 82.86, 82.82, 81.28, 81.25, 80.42, 80.40, 71.19, 70.65, 58.92, 58.68, 34.37, 34.15, 32.30, 32.22, 32.15, 32.05, 28.07, 28.02, 27.94, 25.69 and 25.55. MS (ESI+): 540 (M+Na)$^+$.

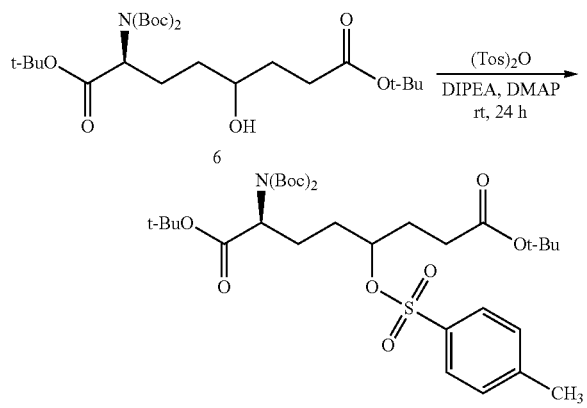

(2S)-di-tert-butyl 2-(bis(tert-butoxycarbonyl)amino)-5-(tosyloxy)octanedioate (7)

To a solution of (2S)-di-tert-butyl 2-(bis(tert-butoxycarbonyl)amino)-5-hydroxyoctanedioate (0.03 g, 0.06 mmol) was added diisopropylethylamine (0.12 mL, 0.69 mmol) and catalytic quantity of 4-dimethyl aminopyridine (~1.0 mg) at room temperature. The resulting reaction mixture was stirred for five more minutes then added solid 4-methylbenzenesulfonic anhydride (0.19 g, 0.58 mmol) at a time and continued stirring for an overnight. The second part of 4-methylbenzenesulfonic anhydride (0.095 g, 0.29 mmol) was added since the starting material was not consumed and the kept the reaction stirring at the room temperature for another 12 h. Finally, the reaction mixture was diluted with ethyl acetate (20 mL) and saturated aqueous NaHCO$_3$ (10 mL) and stirred for 10 minutes. Organic layer was separated, dried over sodium sulfate, filtered and concentrated under reduced pressure. The crude product was purified on 4 g silica gel column (eluent hexanes to 40% ethyl acetate in hexanes) to afford (2S)-di-tert-butyl-2-(bis(tert-butoxycarbonyl)amino)-5-(tosyloxy)octanedioate (diastereomeric mixture, 12 mg, 29.8% yield) as a viscous oil. $^1$H NMR (CDCl$_3$) δ ppm: 7.81 (2d, 2H), 7.35 (m, 2H), 4.60 (m, 2H), 2.46 (s, 3H), 2.35-1.55 (m, 8H), 1.51 (m, 18H), 1.44 (m, 18H). $^{13}$C NMR (CDCl$_3$) d ppm: 171.84, 171.82, 169.28, 169.26, 152.32, 144.57, 134.27, 129.84, 129.82, 127.75, 127.72, 82.91, 82.88, 82.17, 82.0, 81.35, 81.30, 80.50, 58.57, 58.28, 31.25, 30.68, 30.58, 28.29, 28.92, 28.50, 28.08, 28.05, 28.02, 28.00, 27.93, 24.57, 24.30 and 21.65. MS (ESI+): 694 (M+Na)$^+$.

Tritiation:

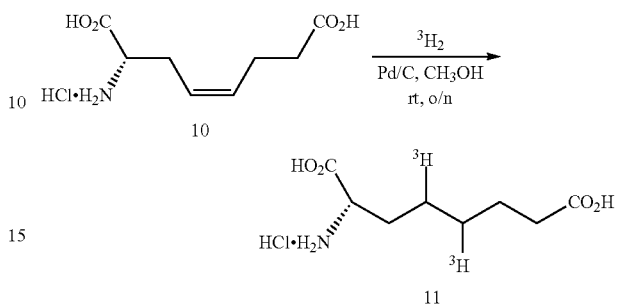

Preparation of (S)-2-Amino 4,5-3H-Suberic Acid

A 50-mL round bottom (RB) flask was purged with nitrogen and charged with (S)-2-amino 4,5-dehydro suberic acid hydrochloride salt (5.0 mg), methanol (4 mL) and 5% palladium on carbon (~1.0 mg dry weight). The RB flask was evacuated, charged with tritium gas (to a pressure of 13 psi or approximately 1.0 atmosphere pressure) and stirred for an overnight at room temperature. After this time, the hydrogen was evacuated and nitrogen charged into the RB flask. The catalyst was removed by filtration through a pad of Celite 545 and the filter cake washed with methanol (10 mL) and water (2.0 mL). The filtrate was concentrated under reduced pressure to afford (S)-2-amino 4,5-$^3$H-suberic acid hydrochloride salt as a white solid.

Example 1

Mouse lymphoma cells (EL4) were cultured with or without 100 μM diethylmaleate for 24 hours, washed in phosphate buffered saline (PBS) divided into aliquots of 5×10$^6$ cells and incubated with [$^3$H]-L-2-aminosuberic acid ($^3$H-L-Asu) without or with inhibitors of the cystine/glutamate transporter for 15 minutes. Cells were then washed 3 times and collected in a 1 ml volume of 1M HCl and transferred to a scintillation vial. 12 ml of Ready Gel scintillation fluid was added to each sample and cell uptake was determined by scintillation counting using a Perkin Elmer Tri-Carb Liquid Scintillation Analyzer. FIG. 1 shows that $^3$H-L-Asu uptake is increased in cells exposed to oxidative stress via DEM treatment. Additionally, more than 95% of uptake is inhibited by cystine/glutamate transporter inhibitors sulfasalazine (SSZ, 500 μM), glutamate (L-GLU, 2.5 mM) and excess unlabeled L-ASU (2.5 mM). This data suggests that $^3$H-Asu uptake in these cells occurs via the cystine/glutamate transporter and is sensitive to oxidative stress.

Example 2

Figure 2:
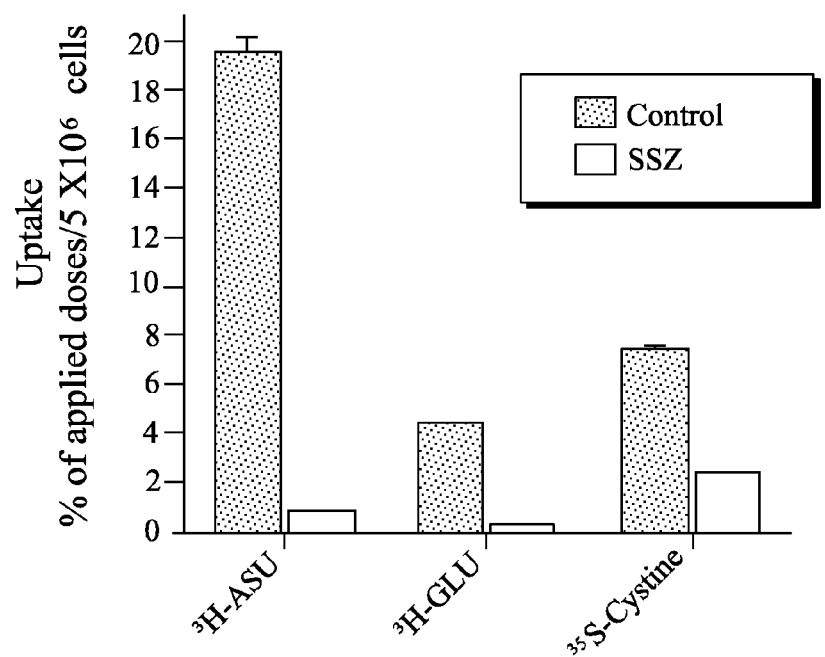
FIG. 2 shows the uptake of each labeled compound in percent of applied dose per sample, and the uptake in the presence of a cystine/glutamate transporter inhibitor sulfasalazine (SSZ).

5×10$^6$ DEM treated EL4 cells were incubated with 0.33 μCi of either [$^3$H]-L-ASU, [$^3$H]-L-GLU or [$^{35}$S]-L-Cystine (with or without 500 μM SSZ) for 15 minutes before being washed three times in PBS and uptake was analyzed via liquid scintillation counting. FIG. 2 shows the uptake of each labeled compound in percent of applied dose per sample, and the uptake in the presence of a cystine/glutamate transporter inhibitor. This data shows that L-ASU uptake is approximately 4.5 times more efficient than L-GLU uptake, which suggests that labeled L-Asu derivatives may result in more promising imaging agents than labeled L-Glu deriviatives. Additionally, both L-ASU and L-GLU uptake is almost completely inhibited by SSZ suggesting that this uptake is predominantly the effect of the cystine-glutamate transporter. L-ASU showed slightly more SSZ inhibition. L-cystine resulted in slightly more uptake as a percentage of the applied dose than L-GLU, however SSZ only inhibited approximately ⅔rds of the uptake, suggesting that ~⅓$^{rd}$ of the uptake detected is due to either another transport system or non-specific binding. Values for relative uptake and % SSZ inhibition are shown in Table 2.

TABLE 2

|  | Uptake relative to $^3$H-GLU | SSZ inhibition (%) |
| --- | --- | --- |
| $^3$H-Asu | 447.0 (±22.1) | 95.8 (±0.17) |
| $^3$H-GLU | 100.0 (±0.6) | 94.6 (±0.61) |
| $^{35}$S-Cystine | 168.8 (±2.0) | 68.7 (±1.76) |

Example 3

Figure 3:
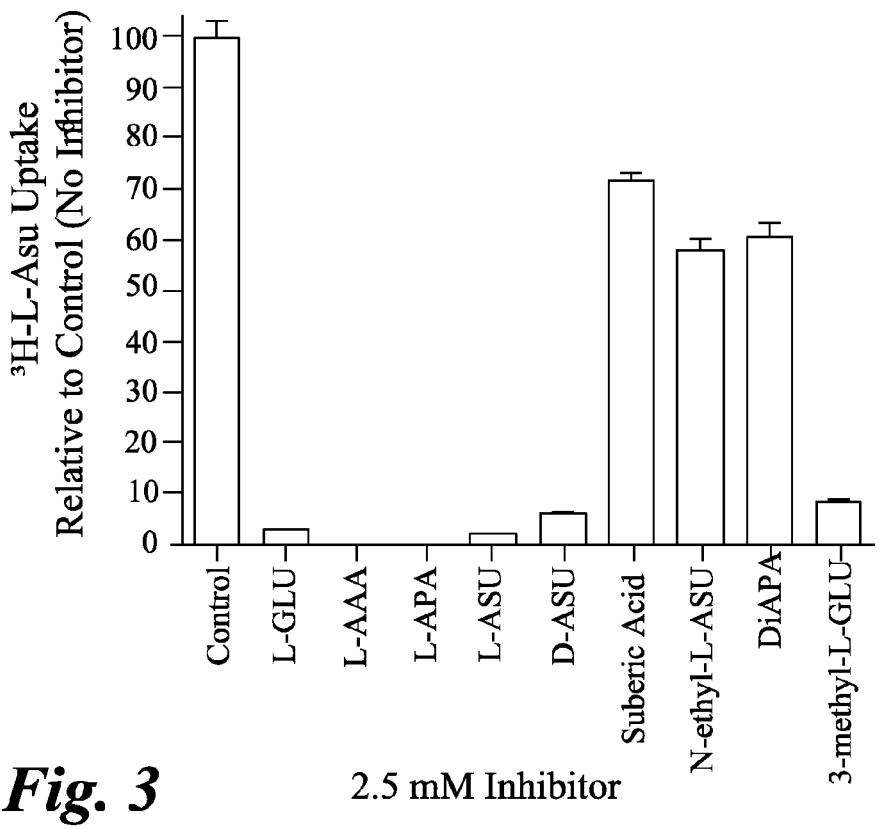
FIG. 3 shows a screen of additional compounds to assess competition for uptake via the cystine/glutamate transporter.

Analysis of unlabeled compounds for their ability to compete for uptake of either $^3$H-GLU or $^3$H-ASU allows selection of compounds that may be transporter substrates and potential leads for imaging agent development. Those compounds that are good substrates for the transporter are expected to result in ≥90% inhibition of uptake at a high concentration (2.5 mM). FIG. 3 shows a screen of additional compounds to assess competition for uptake via the cystine/glutamate transporter. L-GLU, L-aminoadipic acid (L-AAA), L-aminopimelic acid (L-APA), L-ASU, D-ASU and 3 methyl-L-GLU show more than 90% inhibition of $^3$H-L-ASU uptake which suggests that these compounds are adequate competitive inhibitors of the cystine/glutamate transporter. N-Ethyl-L-Asu, suberic acid, diaminopimelic acid (DiAPA) and γ-glutamyl-glycine show less than 45% inhibition, which suggests that they are not good competitive inhibitors of the cystine/glutamate transporter.

Example 4

Figure 4:
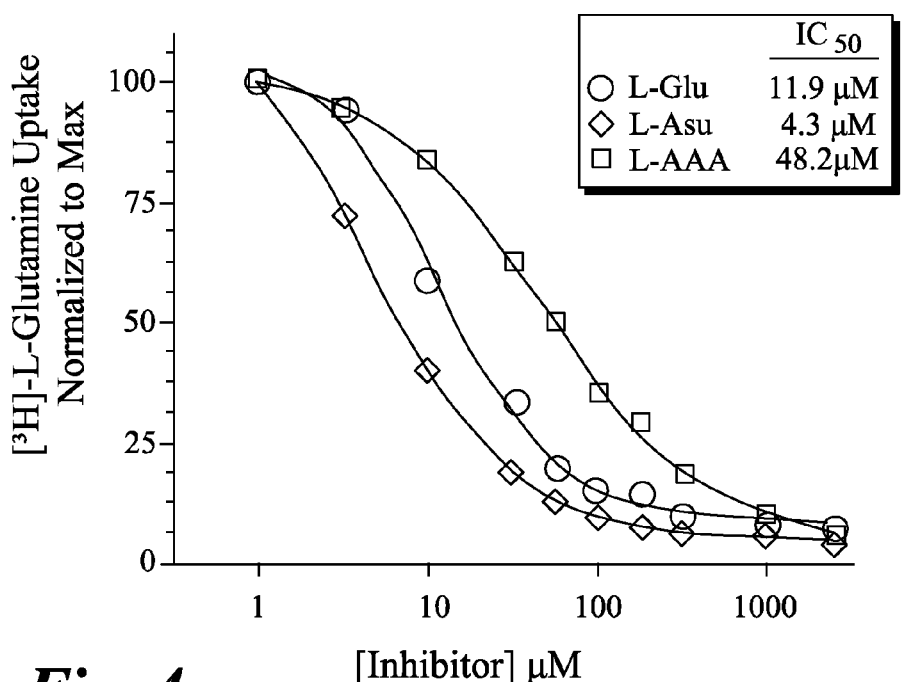
FIG. 4 shows the dose dependent inhibition response of L-glutamate (L-Glu), L-Asu, and L-aminoadipic acid (L-AAA) and D-Asu for $^3$H-L-GLU uptake in DEM treated EL4 cells.

By analyzing the dose response of inhibition we are able to rank compounds with respect to their inhibition of $^3$H-L-Glutamate or $^3$H-L-Aminosuberic acid uptake. FIG. 4 shows the dose dependent inhibition response of L-GLU, L-ASU and L-AAA for $^3$H-L-GLU uptake in DEM treated EL4 cells. In a separate set of experiments it was shown that L-ASU inhibits uptake at a slightly lower dose (IC50=2.9 μM) than L-GLU (IC50=4.7 μM), suggesting that it is a better competitive inhibitor of the cystine/glutamate transporter. However, L-AAA (a known cystine/glutamate transporter substrate, which also has a longer carbon chain than glutamate) requires a higher concentration (IC50=23.9 μM), as does D-Asu (IC50=36.2 μM).

Example 5

Figure 5:
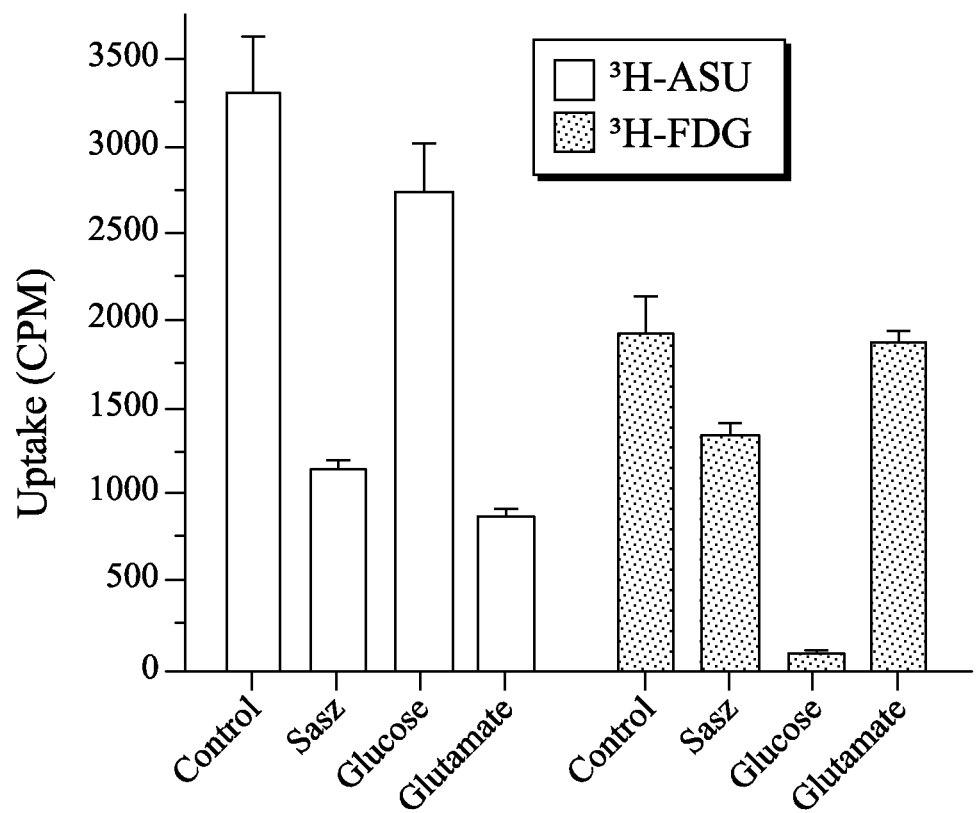
FIG. 5 shows a comparison of uptake of $^3$H-L-Asu and $^3$H-2-deoxy-2-fluoro-glucose ($^3$($^3$H-FDG) in ex vivo EL4 xenograft tumor tissue.

We compared uptake of $^3$H-ASU in tumor tissue ex vivo with uptake of $^3$H-FDG, a tritiated form of the common $^{18}$F-FDG imaging agent. the two agents were matched for specific activity and radioactive dose. 0.33 μCi of agent was incubated with equivalent aliquots of EL4 xenograft tumor tissue slices for 30 minutes (tumors processed with three passes on a McIlwain Tissue chopper, at 500 um steps, and washed with fresh buffer). Slices where washed three times, lysed with 1M HCl and evaluated by scintillation counting. FIG. 5 shows that $^3$H-L-Asu demonstrated 70% more uptake than $^3$H-FDG in these tumor slices.

These agents that are taken up into cells may be used to image cellular oxidative stress in vivo, including without limitation, the imaging of pathologies or conditions that include cellular oxidative stress. Imaging applications that would benefit from these agents include, but are not limited to, chemotherapy treatment monitoring, ischemia/stroke, inflammation, traumatic brain injury and organ transplant monitoring.

Radioisotope labels such as $^3$H $^{18}$F, may be particularly useful for in vivo PET as well as in vitro detection of cellular oxidative stress. While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A cystine/glutamate transporter imaging agent comprising a $^{18}$F labeled derivative of Formula I

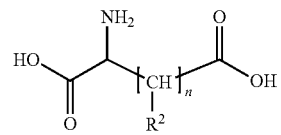

wherein:
Formula I is a L-enantiomeric form;
$R^2$ is independently at each occurrence H and $^{18}$F wherein $^{18}$F is singularly occurring; and
n is 5.

2. A method for imaging a target having a cystine/glutamate transporter comprising:
introducing into the target an imaging agent of claim 1 comprising a $^{18}$F labeled derivative of Formula I

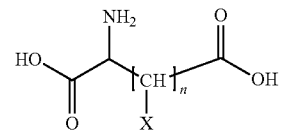

wherein;
X is independently at each occurrence H, and $^{18}$F wherein $^{18}$F is singularly occurring;
n is an integer between 3 and 7; and
detecting the labeled derivative in the target.

3. The method of claim 2, wherein the labeled derivative comprises a compound of Formula II

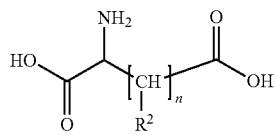

wherein $R^2$ is independently at each occurrence H, $^{18}$F, —$(CH_2)_m R^3$, or —O—$(CH_2)_m R^3$;

$R^3$ is $^{18}$F or wherein $R^2$ is a singularly occurring $^{18}$F n is an integer between 3 and 7; and m is an integer between 1 and 3.

4. The method of claim 3 wherein $R^2$ is $^{18}$F and n is equal to 5.

5. The method of claim 2 wherein the imaging agent is detected in apoptotic cells.

6. The method of claim 2 wherein the imaging agent is detected in cells with high cystine uptake.

7. The method of claim 2 wherein the detecting step comprises detecting the imaging agent using one or more of positron emission tomography (PET), autoradiography, scintillation detection, or a combination thereof.

* * * * *

UNITED STATES PATENT AND TRADEMARK OFFICE
CERTIFICATE OF CORRECTION

PATENT NO. : 8,784,774 B2
APPLICATION NO. : 13/234210
DATED : July 22, 2014
INVENTOR(S) : Webster et al.

Page 1 of 2

It is certified that error appears in the above-identified patent and that said Letters Patent is hereby corrected as shown below:

On the Title Page, item (56), under "OTHER PUBLICATIONS", in Column 1, Line 4, delete "Practicle" and insert -- Practical --, therefor.

On the Title Page, item (56), under "OTHER PUBLICATIONS", in Column 2, Line 34, delete "Clioma" and insert -- Glioma --, therefor.

On the Title Page, item (56), under "OTHER PUBLICATIONS", in Column 2, Line 45, delete "Glutahione" and insert -- Glutathione --, therefor.

In the Drawings,

In Fig. 3, Sheet 2 of 3, delete " Irñhibitor) " and insert -- Inhibitor) --, therefor.

In the Specification,

In Column 2, Line 9, delete "An imaging" and insert -- an imaging --, therefor.

In Column 4, Line 11, delete "or $^3$H:" and insert -- or $^3$H; --, therefor.

In Column 13, Line 3, delete "deriviatives." and insert -- derivatives. --, therefor.

In Column 13, Line 64, delete "agent. the" and insert -- agent. The --, therefor.

Signed and Sealed this
Eighteenth Day of November, 2014

Michelle K. Lee
*Deputy Director of the United States Patent and Trademark Office*

CERTIFICATE OF CORRECTION (continued)
U.S. Pat. No. 8,784,774 B2

In the Claims,

In Column 14, Line 52, in Claim 2, delete "wherein;" and insert -- wherein: --, therefor.

In Column 14, Line 53, in Claim 2, delete "H," and insert -- H --, therefor.

In Column 15, Line 3, in Claim 3, delete "or wherein" and insert -- wherein --, therefor.